United States Patent [19]

Trott

[11] Patent Number: 5,372,604
[45] Date of Patent: Dec. 13, 1994

[54] SUTURE ANCHOR FOR SOFT TISSUE FIXATION

[75] Inventor: Arthur F. Trott, Largo, Fla.

[73] Assignee: Linvatec Corporation, Largo, Fla.

[21] Appl. No.: 78,907

[22] Filed: Jun. 18, 1993

[51] Int. Cl.⁵ .......................................... A61B 17/56
[52] U.S. Cl. .................................. 606/232; 411/922; 606/72; 606/205
[58] Field of Search ............. 606/232, 72, 74, 75, 606/205–211, 142, 143, 139; 411/460, 466, 922

[56] References Cited

U.S. PATENT DOCUMENTS

| | | | |
|---|---|---|---|
| 1,519,502 | 12/1924 | Nalle | 411/922 X |
| 1,721,626 | 7/1929 | Higley | 411/922 X |
| 3,003,155 | 10/1961 | Mielzynski et al. | |
| 3,699,969 | 10/1972 | Allen | |
| 3,862,453 | 1/1975 | Widdifield | |
| 4,244,370 | 1/1981 | Furlow et al. | |
| 4,245,545 | 1/1981 | Freeman | |
| 4,632,100 | 12/1986 | Somers et al. | |
| 4,721,103 | 1/1988 | Freedland | 606/72 |
| 4,738,255 | 4/1988 | Goble et al. | |
| 4,741,330 | 5/1988 | Hayhurst | |
| 4,750,492 | 6/1988 | Jacobs | |
| 4,778,468 | 10/1988 | Hunt et al. | |
| 4,834,752 | 5/1989 | Van Kampen | |
| 4,898,156 | 2/1990 | Gatturna et al. | |
| 4,899,743 | 2/1990 | Nicholson et al. | |
| 4,909,974 | 3/1990 | Toncelli | |
| 4,924,865 | 5/1990 | Bays et al. | |
| 4,946,468 | 8/1990 | Li | |
| 4,968,315 | 11/1990 | Gatturna | |
| 5,037,422 | 8/1991 | Hayhurst et al. | |
| 5,041,129 | 8/1991 | Hayhurst et al. | |
| 5,046,513 | 9/1991 | Gatturna et al. | 606/232 X |
| 5,078,730 | 1/1992 | Li et al. | |
| 5,100,417 | 3/1992 | Cerier et al. | |
| 5,102,421 | 4/1992 | Anspach, Jr. | |
| 5,139,520 | 8/1992 | Rosenberg | |
| 5,141,520 | 8/1992 | Goble et al. | |
| 5,156,616 | 10/1992 | Meadows et al. | |
| 5,176,682 | 1/1993 | Chow | 606/232 X |
| 5,192,303 | 3/1993 | Gatturna et al. | |
| 5,203,787 | 4/1993 | Noblitt et al. | 606/72 X |
| 5,207,679 | 5/1993 | Li | |
| 5,217,486 | 6/1993 | Rice et al. | 606/232 |
| 5,224,946 | 7/1993 | Hayhurst et al. | |
| 5,236,445 | 8/1993 | Hayhurst et al. | 606/232 |
| 5,273,024 | 12/1993 | Menon et al. | |
| 5,273,529 | 12/1993 | Idowu | |
| 5,273,545 | 12/1993 | Hunt et al. | |
| 5,275,609 | 1/1994 | Pingleton et al. | |
| 5,275,612 | 1/1994 | Bales, Jr. | 606/205 |

Primary Examiner—Peter A. Aschenbrenner

[57] ABSTRACT

A method and apparatus for anchoring suture to bone includes an anchor formed by twisting a wire to provide a loop with two legs extending distally from the twist. Each leg bends outwardly through 180° to define respective knee segments between inner and outer leg segments, the outer leg segments terminating in sharp points for penetrating a bone tunnel wall. The outer leg segments are initially parallel and define an anchor width smaller than the bone tunnel diameter, thereby permitting the anchor to be inserted into and removed from the tunnel. The anchor is deployed with an insertion tool arranged to deformably pivot the outer leg segments about the knee segments, thereby causing the pointed ends to penetrate the tunnel wall in response to applied withdrawal forces. The anchor wire may be assembled on an anchor sleeve through which the loop projects proximally while the outer leg segments reside in wire relief recesses defined in the sleeve periphery. The insertion tool selectively forces the sleeve against the inside of the knee segments while engaging the loop to thereby deformably pivot the outer leg segments. The insertion tool may include resiliently spaced jaws for engaging the wire loop, the jaws being disposed at the distal end of a rod selectively retractable into a tube to force the jaws closed. Further retraction of the rod applies the axial force for bending the wire legs.

23 Claims, 3 Drawing Sheets

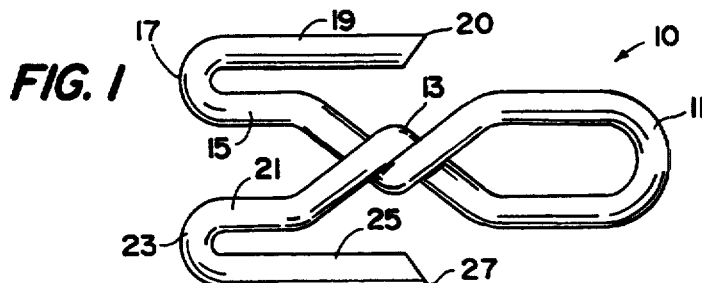
FIG. 1
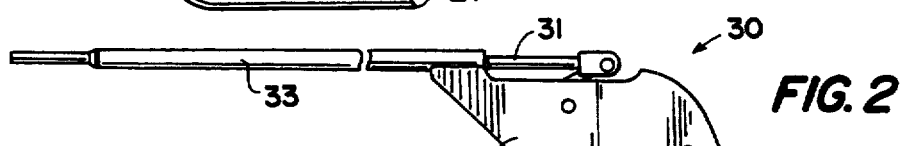
FIG. 2
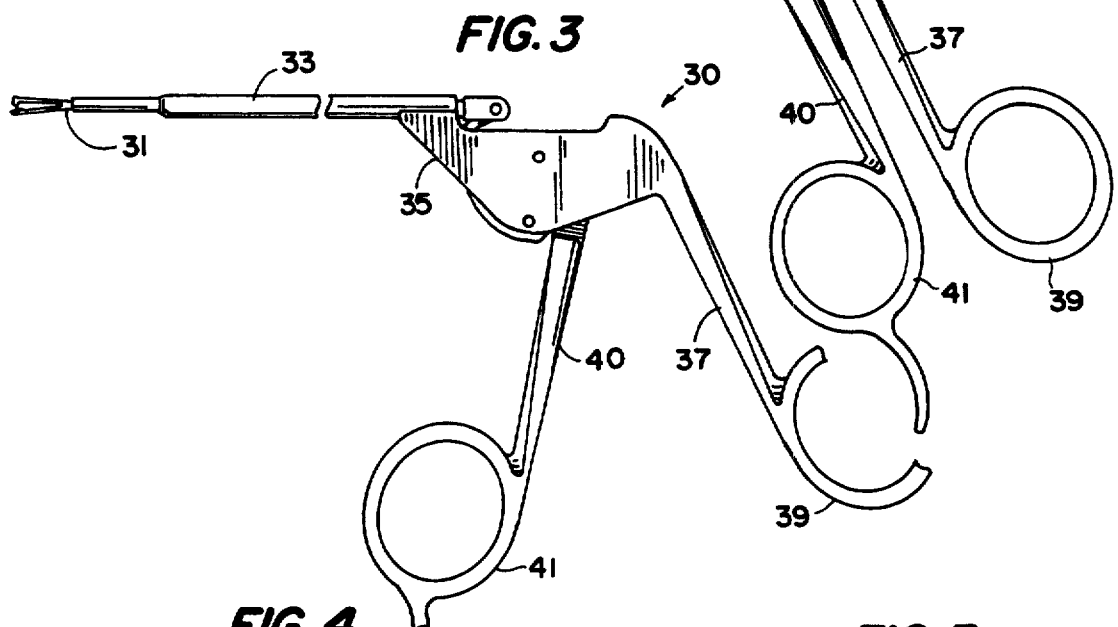
FIG. 3
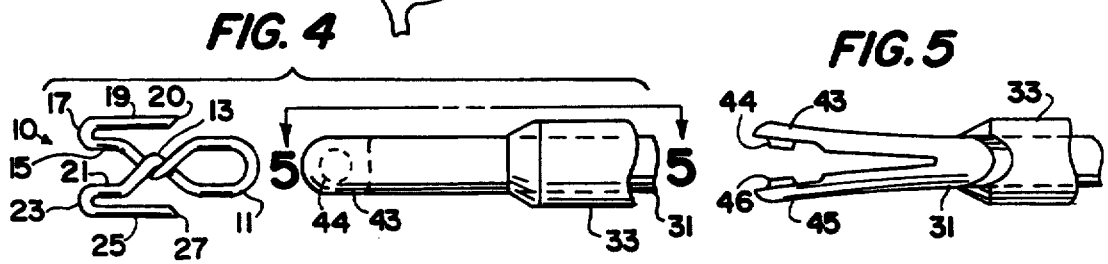
FIG. 4
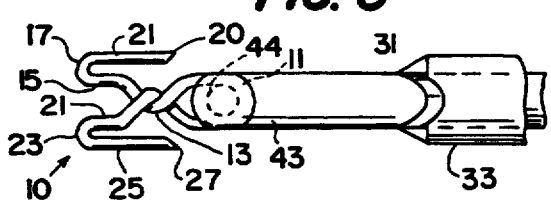
FIG. 6
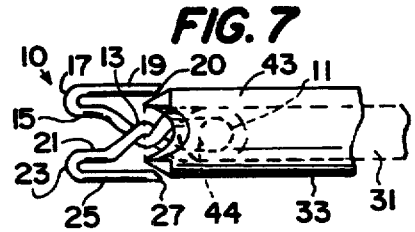
FIG. 5
FIG. 7

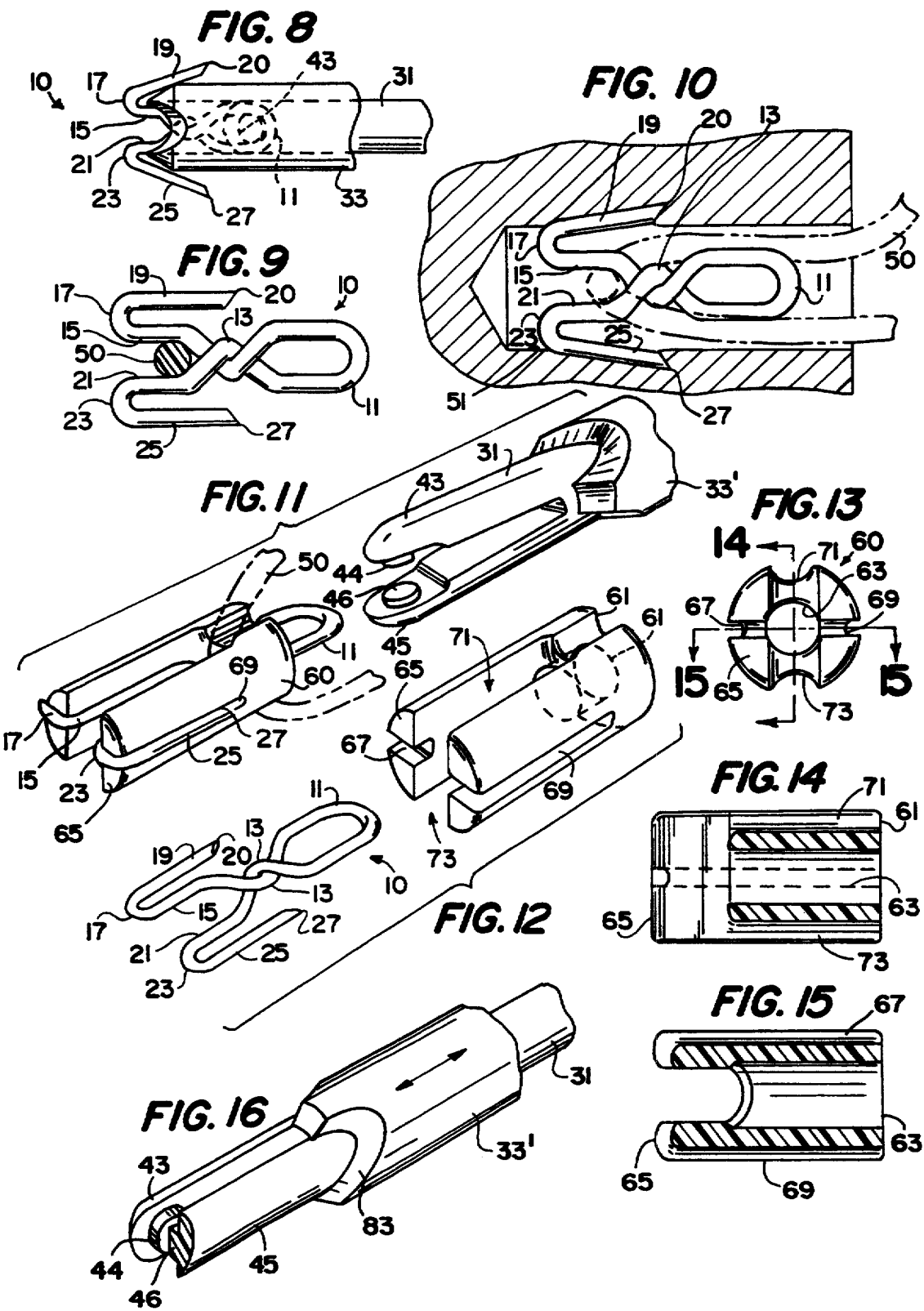

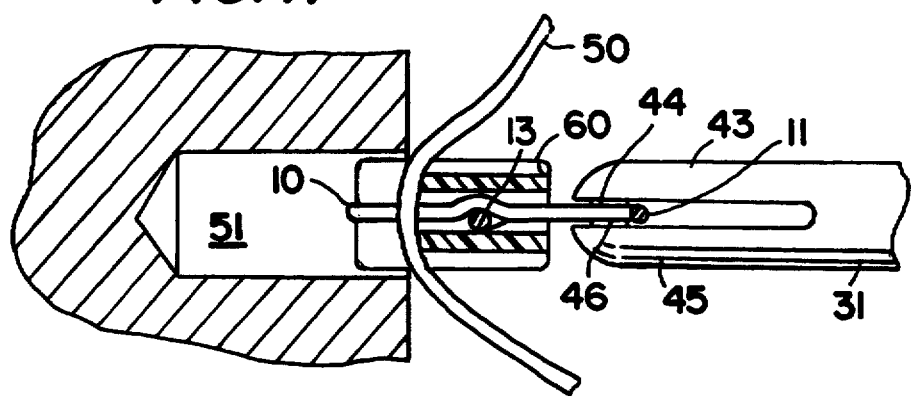
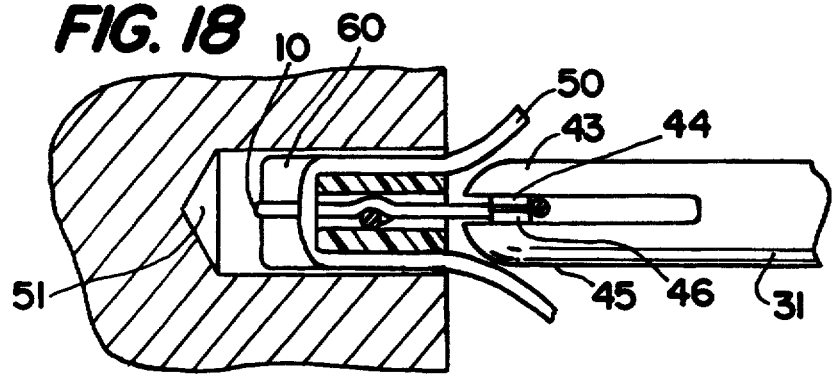
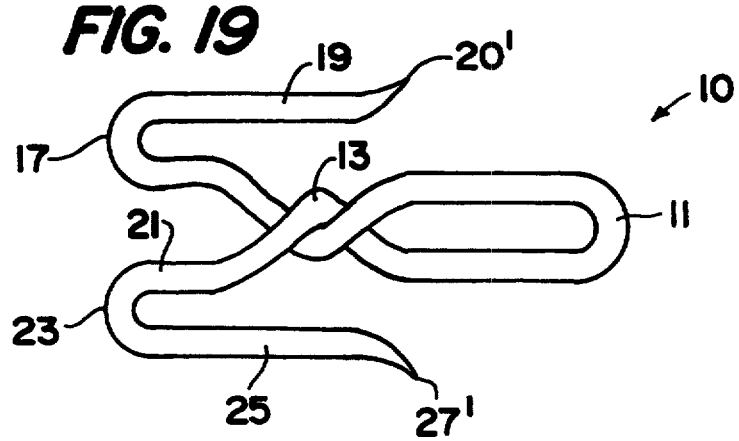

SUTURE ANCHOR FOR SOFT TISSUE FIXATION

BACKGROUND OF THE INVENTION

Technical Field

This invention pertains to methods and apparatus utilized in surgical procedures involving fixation of soft tissue to bone tissue and, more particularly, to a novel method and apparatus for anchoring sutures to bone tissue to permit the aforesaid fixation.

DISCUSSION OF THE PRIOR ART

As part of various endoscopic or arthroscopic surgical procedures, it is necessary to permanently attach a suture to bone tissue. For example, in certain procedures requiring suturing of soft tissue (e.g., muscle, cartilage, tendons, ligaments, etc.) to bone tissue, the suture must be anchored to the bone tissue before suturing can proceed. The prior art includes numerous suture anchors adapted to be secured in pre-drilled holes or tunnels in the bone tissue, and most of these anchors have one or more disadvantageous characteristics. Some prior art suture anchors are required to be hammered into the bone tunnel. These anchors are exemplified by U.S. Pat. No. 5,102,421 (Anspach, Jr.); U.S. Pat. No. 5,141,520 (Goble et al); and U.S. Pat. No. 5,100,417 (Cerier et al). Hammering (or impacting as it is often described) has the disadvantage of potential trauma and damage to surrounding bone tissue, and has limited applicability where the location of the bone tunnel is not axially aligned with an arthroscopic portal to permit transmission of the impacting force through an impactor to the anchor.

Some suture anchors are threadedly mounted in the bone tunnel, as exemplified by U.S. Pat. No. 5,156,616 (Meadows et al) and U.S. Pat. No. 4,632,100 (Somers et al). The screw insertion procedure tends to be time-consuming in that a pilot hole must first be drilled into the bone and then the hole may have to be tapped to receive the screw.

Many suture anchors involve an insertion procedure wherein the inserter device must partially enter the bone tunnel, thereby requiring a larger diameter tunnel than would be necessary for the anchor alone. Examples of such suture anchors are found in U.S. Pat. No. 5,037,422 (Hayhurst et al); U.S. Pat. No. 4,741,330 (Hayhurst); U.S. Pat. No. 4,968,315 (Gatturna) and U.S. Pat. No. 4,899,743 (Nicholson et al).

Most of the foregoing exemplar prior art suture anchors suffer from the disadvantage of being automatically deployed upon initial insertion into the bone tunnel. Specifically, such anchors typically have permanently projecting barbs, or the like, that are forced into the tunnel during initial insertion and preclude proximally directed movement in the tunnel after at least one barb engages the surrounding bone tissue. It sometimes happens that a particular tunnel turns out to be unsuitable, either because of location or configuration, but the surgeon does not recognize this until after the anchor has been inserted. With most prior art anchors there is no possibility of removing the inserted anchor; thus, a new tunnel must be drilled and a second anchor inserted. Accordingly, two (or possibly more) anchors may be left at the surgical site, only one of which is functional. This problem is addressed in U.S. Pat. No. 5,176,682 (Chow) wherein a suture anchor is disclosed as having normally retracted fins capable of being selectively projected radially to engage the bone tunnel walls in a barb-like manner. Selective projection of the fins is effected by hammering a pin axially through the anchor to force the fins radially outward. Prior to hammering the pin, the inserted anchor is readily removable from the bone tunnel, thereby permitting the surgeon to test the adequacy of the drilled tunnel and its location. If the tunnel is unsatisfactory, the anchor can be removed, rather than being left in place. Although this technique solves the problem of having an unused anchor left in an unsatisfactory tunnel, it has some other disadvantages. Specifically, permanent installation of the anchor requires tools (i.e., a hammer and impactor) that are separate and apart from the inserter. Additionally, during impacting, the pin may be inadvertently driven entirely through the anchor and thereby damage bone tissue at the closed end of the tunnel.

OBJECTS AND SUMMARY OF THE INVENTION

It is therefore an object of the present invention to provide improved methods and apparatus for anchoring suture to bone.

It is another object of the invention to provide a suture anchor capable of being temporarily inserted into a bone tunnel to determine the desirability of the site, and then easily actuated for permanent deployment.

A further object of the invention is to provide a suture anchor that can be inserted and positively engaged in a bone tunnel without requiring hammering of the anchor or threading the tunnel.

It is yet another object of the present invention to provide a method and apparatus for securing a suture anchor in a bone tunnel without requiring the tunnel diameter to be larger than necessary to accommodate the anchor.

In accordance with the present invention, a suture anchor wire is configured from a deformable wire bent to provide a loop at the approximate center of the wire length. The loop constitutes the proximal end of the anchor. The wire is twisted to close off the loop at a twist juncture from which two legs extend generally distally and then bend away from one another through approximately 180° each to extend in a proximal direction along opposite transverse sides of the anchor. Ends of the wire are cut on a bias to define sharp points at the outer transverse sides of the leg ends. The 180° bend in each leg forms a U-shaped knee dividing the leg into substantially parallel inner and outer leg segments.

An anchor insertion tool includes an elongated hollow outer tube and an inner tube telescopically movable therein. Jaws at the distal end of the inner tube include one or more projections configured to permit the anchor wire loop to be selectively engaged between the jaws. With the anchor engaged, a generally annular actuator edge of the outer tube of the inserter tool, or of a sleeve disposed about the inner tube and extending forwardly of the outer tube, is axially spaced from the anchor wire legs. The actuator edge has an outside diameter made smaller than the transverse spacing between the outward sides of the outer leg segments, but larger than the transverse spacing between the inward sides of the outer leg segments. Suture or similar material can be looped about the twist between the two inner leg segments of the anchor wire and pulled back proximally before the engaged anchor is inserted into a pre-drilled tunnel in bone tissue. The transverse spacing between the proximally-directed anchor leg segments permits the anchor to be moved freely into and out of the tunnel. When the anchor wire is positioned as desired, the actuator inner tube is retracted into the outer tube, thereby causing the actuator edge to move distally relative to the anchor wire and into the space between the leg segments of each wire leg. As the actuator edge moves between the leg segments it forces the outer segments outwardly, thereby deforming the wire knee so that the pointed ends of the outer segments engage the wall in the bone tunnel. The entire tool can then be pulled in the proximal direction, with the anchor loop still engaged by the actuator, to cause the pointed ends of the now outwardly bent outer leg segments of the anchor to firmly engage the wall of the tunnel. Disengagement of the inserter tool from the anchor wire is effected by opening the jaws of the inner tube to disengage the wire loop. The tool can then be removed from the surgical site and the suture remains in the bone tunnel, firmly engaged about the anchor wire twist.

In one embodiment, the anchor also includes a sleeve on which the anchor wire, as described above, is mounted. The anchor sleeve has an open distal end and a proximal end wall having a central opening. The wire is mounted with its loop protruding rearwardly through the hole in the proximal end wall, and with its U-shaped knee bent over the edge of the open distal sleeve end. Recessed channels extend longitudinally along the outside of the sleeve from its distal end to receive the outer leg segments of the anchor wire. When thusly received, the entire diametric thickness of the outer leg segment is recessed in the channel. As in the first described embodiment, the rearward projecting wire loop is engageable between the jaws of the insertion tool. During deployment, instead of spreading the outer leg segments directly by means of the distal end of the insertion tool outer tube, the distal end of the tube is forced against the proximal end wall of the anchor sleeve. The sleeve, in turn, is thusly movable distally relative to the engaged anchor wire to force the outer leg segments of the wire radially outward. In this embodiment the anchor sleeve remains in the bone tunnel along with the anchor wire after deployment.

These and other objects, features and many of the attendant advantages of the present invention will be appreciated more readily as they become better understood from a reading of the following description considered in connection with the accompanying drawings wherein like parts in each of the several figures are identified by the same reference numerals.

BRIEF DESCRIPTION OF THE DRAWINGS

FIG. 1 is a view in plan of an anchor wire constructed in accordance with one embodiment of the present invention.

FIG. 2 is a side view, partly broken, of an inserter tool utilized in connection with the anchor wire according to the present invention showing the tool in its deployment position.

FIG. 3 is a side view, partly broken, of the inserter tool shown in its pre-deployment position.

FIG. 4 is a top view in plan of the combination of the anchor wire of FIG. 1 and the distal end of the insertion tool of FIG. 2, the combination being shown prior to engagement of the anchor wire.

FIG. 5 is a side view in elevation of the distal end of the insertion tool taken along lines 5—5 of FIG. 4.

FIG. 6 is a top view in plan of the anchor wire and the distal end of the insertion tool showing the anchor wire engaged prior to deployment and the inner tube of the insertion tool fully extended.

FIG. 7 is a top view in plan of the anchor wire and the distal end of the insertion tool showing the anchor wire in its inserted but non-deployed position and the inner tube of the insertion tool partially retracted.

FIG. 8 is a top view in plan of the anchor wire and the distal end of the insertion tool showing the anchor wire fully deployed and the inner tube of the insertion tool fully retracted.

FIG. 9 is a top view in plan of the anchor wire during as it appears prior to insertion into a bone tunnel and showing a suture engaged by the anchor wire.

FIG. 10 is a top view in plan of the anchor wire fully deployed in a bone tunnel and showing a suture engaged by the anchor wire and retained in the bone tunnel.

FIG. 11 is a view in perspective of a second embodiment of the anchor of the present invention utilizing an anchor sleeve in combination with the anchor wire, and an insertion tool for engaging the anchor wire.

FIG. 12 is an exploded view in perspective of the anchor wire and anchor sleeve of FIG. 11.

FIG. 13 is a distal end view in elevation of the anchor sleeve.

FIG. 14 is a view in section taken along lines 14—14 of FIG. 13.

FIG. 15 is a view in section taken along lines 15—15 of FIG. 13.

FIG. 16 is a view in perspective of the insertion tool of FIG. 11.

FIG. 17 is a side view in elevation of the anchor assembly of FIG. 11 engaged by the insertion tool immediately prior to insertion into a bone tunnel.

FIG. 18 is a side view in elevation of the anchor assembly of FIG. 11 and the insertion tool showing the anchor assembly partially inserted into a bone tunnel.

FIG. 19 is a view in plan of another anchor wire embodiment of the present invention.

DESCRIPTION OF THE PREFERRED EMBODIMENTS

Referring specifically to FIG. 1, an anchor wire 10 is bent and twisted to provide an engagement loop 11 positioned approximately at the center of the length of the wire. Engagement loop 11 constitutes the proximal end of the anchor device and, in the preferred embodiment, has a generally elliptical configuration with its major axis extending longitudinally. The forward end of loop 11 terminates in a twist 13 formed in wire 10, the preferred twist being 180° about the longitudinal axis of the anchor to close off the loop from the distal end of the anchor. Specifically, each leg of the wire bends through approximately 90° to form twist 13. Extending forwardly from twist 13 are two legs, each having a 180° outward bend or knee 17, 23 to separate inner and outer leg segments. Specifically, one leg includes an inner segment 15 extending forwardly from twist 13 to knee 17, and an outer segment 19 extending rearwardly from knee 17 and substantially parallel to inner segment 15. Outer segment 19 constitutes the radially outwardmost part of one side of the anchor wire and terminates in a pointed end 20 formed by cutting the wire end on a bias in a proximal and outward direction. The other leg is a substantially mirror image (about the anchor longitudinal axis) of the first leg and has corresponding inner segment 21, knee 23, outer segment 25 and pointed end 27. The forward ends of knees 17 and 23 are longitudinally coextensive and define the distal end of the anchor wire.

Anchor wire 10 is preferably a metal wire, typically stainless steel, that is bendable but not significantly resilient. Accordingly, if, in the manner described below, outer leg segments 19 and 25 are bent outwardly about respective knees 17 and 23 to form some angle other than 180° with the inner segments 15 and 21, the resulting deformation of the anchor wire remains set after the bending force is removed.

In an exemplar embodiment of anchor wire 10, the wire has a round transverse cross-section with a diameter of 0.015". The overall length (i.e., from the proximal end of loop 11 to the distal ends of knees 17, 23) of the formed anchor wire is 0.220", with the outer leg segments each occupying 0.100" of that length. The maximum transverse width of the anchor wire between the outermost parts of outer leg segments 19 and 25 is 0.110". The transverse space between inner leg segments 15 and 21 is 0.030". Likewise, the transverse space between the long sides of loop 11 is 0.030". The angle of the bias cut in outer leg segments 19 and 25 to form respective points 20 and 27 is 30°. Again, it is to be noted that these dimensions are for purposes of example only and are not limiting on the scope of the present invention.

An anchor insertion tool 30 is illustrated in FIGS. 2 and 3 includes concentric inner and outer tubes 31 and 33, respectively. Outer tube 33 is fixedly secured to and extends forwardly from an actuator housing 35. A thumb-engaging handle arm 37 is fixedly secured to the proximal end of housing 35, extending rearwardly and transversely therefrom and terminating in a thumb-receiving loop 39. A finger-engaging handle arm 40 is pivotably secured within housing 35 and extends transversely forwardly therefrom to form an acute angle with arm 37. A finger-receiving loop 41 terminates the free end of arm 40. In a conventional manner, arm 40 is linked within housing 35 to the proximal end of inner tube 31 such that forward movement of arm 40 relative to arm 37 (i.e., increased angular separation) results in coaxially forward displacement of inner tube 31 within outer tube 33. Likewise, rearward movement of arm 40 (i.e., decreasing the angular separation) causes inner tube 31 to move axially rearward within outer tube 33. In this manner, the distal end of inner tube 31 may be selectively projected beyond the distal end of tube 33, or fully retracted within the outer tube. The diameters and lengths of tubes 31, 33 are such to permit their distal ends to be inserted through an endoscopic surgical portal and positioned at a surgical site. The particular embodiment illustrated herein is best suited for arthroscopic procedures.

The distal end of inner tube 31 terminates in a pair of resiliently spaced jaws 43 and 45. When inner tube 31 is fully extended forwardly, jaws 43 and 45 are exposed and maximally separated. In this position the spacing between the outside surfaces of the jaws exceeds the inner diameter of outer tube 33. As the inner tube is retracted into the outer tube, the interior wall of outer tube 33 serves as a cam to gradually urge jaws 43 and 45 together in opposition to their resilient separation bias. The interior or mutually facing surfaces of jaws 43 and 45 have respective engagement pins 44 and 46 projecting inwardly toward one another. In the fully open position of the jaws (i.e., in the fully extended position of inner tube 31), the spacing between engagement pins 44 and 46 is at least equal to the diameter of the wire used for anchor wire 10. The cross-sectional shape of pins 44 and 46 (i.e., transversely of their mutual projection directions) is chosen to permit the pins to fit into the loop 11 of the anchor wire when the jaws are closed. Preferably, the engagement pins are cylinders having a radius equal to or just slightly smaller than the radius of curvature of the proximal end of the interior portion of wire loop 11.

Referring to FIGS. 4 and 5, when it is desired to load anchor wire 10 onto insertion tool 30, inner tube 31 is extended to its most distal position relative to the outer tube by angularly separating handle arms 37 and 40 to their maximum separation. Jaws 43 and 45 are resiliently spread and pins 44 and 46 thereby are spaced from one another. The anchor wire loop may then be inserted between jaws 43, 45 and their engagement pins 44, 46. As illustrated in FIG. 6, the jaws may be closed, bringing engagement pins 44, 46 into contact through anchor wire loop 11. Closure of the jaws is effected by pivoting handle arm 40 partway toward handle arm 37, thereby causing partial retraction of inner tube 31 into outer tube 33. This retraction, in turn, causes the distal edge of the outer tube to force jaws 43 and 45 together in opposition to their resilient separation bias.

To ready the anchor wire for insertion into a bone tunnel, inner tube 31 is further retracted into outer tube 33, as illustrated in FIGS. 7 and 9, until the loaded anchor wire is disposed with the proximal end of loop 11 abutting the distal end of outer tube 33. In this position, a suture 50 can be disposed with an intermediate portion of its length between inner leg segments 15 and 21 and at the distal end of wire twist junction 13. The two ends of suture 50 are pulled rearwardly to extend along the outer tube 33 of the insertion tool. Suture 50 and the anchor wire 10, engaged by the insertion tool, can then be inserted into a pre-drilled bone tunnel 51. The bone tunnel diameter is substantially equal to or slightly larger than the maximum transverse spacing between the outer edges of outer legs segments 19 and 25 to readily permit insertion of the entire anchor wire and the distal end of the insertion tool into the bone tunnel. With the anchor wire thusly inserted in the tunnel, the surgeon can determine whether or not the tunnel and its location are satisfactory for the contemplated soft tissue anchoring procedure. If the bone tunnel is not satisfactory, the insertion tool and the engaged anchor wire may be readily withdrawn from the tunnel and inserted into a new tunnel appropriately drilled and positioned.

If the bone tunnel is determined to be satisfactory for the contemplated procedure, the anchor wire may be permanently deployed. In particular, and as illustrated in FIGS. 8 and 10, the outer leg segments 19, 25 of the inserted anchor wire are forced outwardly by fully retracting inner tube 31 into outer tube 33 while pulling rearwardly on the insertion tool and, in turn, on the engaged anchor wire. As the inner tube is retracted, the interior sides of knees 17 and 23 move axially toward the distal edge of outer tube 33. The outer tube end begins wedging between inner leg segment 15 and outer leg segment 19, and between inner leg segment 21 and outer leg segment 25, thereby causing the outer leg segments to bend outwardly about their respective knees. Pointed wire ends 20 and 27 diverge by virtue of this bending and dig into the wall of the bone tunnel as the assembly is pulled in a rearward direction. When sufficient resistance to rearward movement is encountered, the anchor wire is deemed properly implanted and the insertion tool can be disengaged from the anchor wire loop 11. This disengagement is effected by moving inner tube 31 proximally to permit jaws 43 and 45 to resiliently separate and release wire loop 11. The insertion tool may then be fully withdrawn from the surgical site, leaving the anchor wire firmly positioned within the bone tunnel and suture 50 looped around the anchor wire. The 180° twist 13 in the anchor wire prevents the suture from being drawn into loop 11 when the ends of the suture are pulled to achieve desired tension.

It is to be noted that, although the preferred embodiment of the insertion tool includes respective engagement pins secured to the jaws 43 and 45, other jaw configurations are possible and fall within the scope of the present invention. For example, only one of the jaws may have a projecting pin configured to engage the opposing jaw when the jaws are closed. Alternatively, the opposing jaw may have a recess or bore defined therethrough in position to receive the engagement pin from the first-mentioned jaw. The configurations of the engagement pins need not be cylindrical; rather, any configuration capable of serving the functions described above is appropriate for the engagement pins.

Likewise, the specific manner by which the jaws are opened and closed should not be a limiting feature of the invention. In particular, the preferred insertion tool described above effects closure of the jaws by withdrawing the resiliently spaced jaws into an outer tube. Rather than providing the illustrated inner tube and outer tube combination, a single tube may be provided with non-resilient jaws formed at its distal end. One of the jaws would be pivotable relative to the tubes so as to selectively close the jaws in a manner similar to that employed for arthroscopic graspers and cutters well known in the prior art. An outer sleeve may then be disposed over the distal end of the insertion tool to be selectively axially movable relative to the jaws to bend the outer leg segments of the anchor wire in a manner described.

An alternative embodiment of the anchor assembly and insertion tool are illustrated in FIGS. 11-18 to which specific reference is now made. In this embodiment the anchor assembly includes anchor wire 10, configured as described above, and a biocompatable anchor sleeve 60. The anchor sleeve 60 has a generally cylindrical configuration with a proximal end wall 61 having a central hole or opening 63 defined therethrough. The diameter of hole 60 is sufficient to permit loop 11 of the anchor wire to project proximally therethrough when the anchor wire is received in sleeve 60 in the manner described below. The opposite or distal end 65 of sleeve 60 is open to receive the anchor wire. Longitudinally extending wire relief channels or recesses 67, 69 are defined in the outer surface of sleeve 60 and extend along the entire length of the sleeve. Channels 67 and 69 are disposed at 180°-spaced locations about the sleeve circumference and are sufficiently deep to receive most, if not all, of the diametric thickness of respective outer leg segments 19 and 25. That is, anchor wire 10, when received in sleeve 60, has the inside surfaces of its knees 17 and 23 disposed in abutting relation with the distal edge of the sleeve. Further, the natural spacing between the outermost edges of inner leg segments 15 and 21 is greater than the inner diameter of sleeve 60. Accordingly, sleeve 60 is retained on anchor wire 10 by a forced fit created by the limited resilience of the anchor wire. In the preferred embodiment, distal end 65 has a pair of recesses 66, 68 serving as extensions of respective channels 67, 69 to receive the entire thickness of respective knees 17 and 23. In this received position of the anchor wire, inner leg segments 15, 21 and twist junction 13 are disposed inside sleeve 60.

At two 180°-spaced locations, spaced 90° from wire relief channels 67 and 69, the wall of sleeve 60 is completely removed along the entire sleeve length. The resulting open spaces 71, 73 are continued as respective arcuate recesses 75, 77 defined in the circumferential edge of proximal end wall 61. Spaces 71, 73 serve as suture relief spaces through which suture 50 extends when looped about the proximal end of wire twist 13 between inner leg segments 15 and 21.

The insertion tool 80 employed with the anchor assembly of wire 10 and sleeve 60 may be substantially the same tool described above. As shown in FIGS. 11-18, the outer tube 33' of the tool may have a pair of 180°-spaced slots 81, 83 cut through the entire tube wall thickness and extending a short distance rearward from the outer tube distal end. The suture ends thus extend through spaces 71, 73 and recesses 75, 77 to reside along the slots 81 and 83.

The operation of the anchor assembly of FIGS. 11-18 is similar to that described above in relation to FIGS. 1-10. Anchor wire loop 11, exposed through sleeve hole 63, is engaged in the same manner between jaws 43 and 45, and the sequence of deployment proceeds as previously described with two significant exceptions. First, instead of the outer leg segments 19 and 25 being deformably bent directly by the distal end of the outer tube 33' upon retraction of the inner tube, the outer tube distal end urges sleeve 60 forwardly relative to the anchor wire. The distal end of the sleeve thus deformably bends the outer leg segments of the wire outwardly under the urging of the distal end of the outer tube as the inner tube retracts.

A second significant distinction resides in the fact that biocompatable sleeve 60 may remain deployed with the anchor wire in the bone tunnel. The forced fit between the sleeve and the inner leg segments 15 and 21 assures that the sleeve will not become disengaged. Of course, the sleeve can be designed to be removed after deployment of the wire, if desired.

Sleeve 60 is made of any suitable bio-compatible metal or plastic material. In an exemplar embodiment, the sleeve has a length of 0.157" and an outside diameter of 0.100". Hole 63 in proximal end wall 61 has a diameter of 0.060" which is substantially equal to the maximum transverse dimension of anchor wire loop 11. Channels 67 and 69 are generally semi-cylindrical with a depth of 0.015", while spaces 71, 73 each subtend a circumferential angle on the order of 60°. The transverse space between interior walls across spaces 71, 73 is 0.040".

It may be desirable, in some instances, to configure the anchor wire in the manner illustrated in FIG. 19 wherein anchor wire 10' is configured to have its pointed ends 20', 27' curved outwardly and way from the longitudinal axis of the anchor. This curvature at the tips of the anchor facilitates penetration into the bone upon outward bending of outer segments 19 and 25 during deployment. In all other respects anchor wire 10' is substantially the same as anchor wire 10.

It will be understood that some of the specific details of the exemplary embodiments described above are not limiting on the scope of the invention. In particular, the feature of primary importance in the anchor is the presence of two or more wire legs capable of being deformably bent outward while in a bone tunnel to permit their pointed ends to penetrate the bone tunnel wall upon being pulled proximally toward the tunnel opening. On the other hand, prior to being bent, the wire legs are retracted such that the maximum transverse dimension of the anchor permits it to be readily inserted into and removed from the tunnel. In this regard, the anchor may comprise only the wire, or the wire engaged by a biocompatable anchor sleeve (both as described above); or it may comprise a body of biocompatable metal or plastic material having the bendable pointed legs embedded therein or otherwise secured at the distal end of the body, and with a loop or other anchor engagement structure at the proximal end of the body. The configuration of the anchor body is not, of itself, critical to the invention, although certain configurations, such as those described herein, are more advantageous than others. The key features, again, are the fact that the legs are deformable to effect deployment while the anchor is in the bone tunnel to permit the anchor to be removed after insertion but prior to bending for deployment, a passage for engaging a suture looped about or through the anchor, and a mechanism for engaging the anchor with a removable insertion tool capable of selectively deploying the anchor in the tunnel by causing the legs to deformably bend outwardly without hammering or impacting the anchor. The specific insertion tool configurations described herein, although particularly advantageous, can also be varied within the scope of the invention. The key features of the tool are the capability of engaging the anchor for selective insertion into and removal from the bone tunnel, and the capability of selectively deploying the anchor by causing deformation of the anchor legs. It should also be noted that inner tube 31 of the illustrated insertion tool may be any rod-like member, whether or not tubular.

From the foregoing description it will be appreciated that the invention makes available a novel suture anchor for soft tissue fixation characterized by being removable from a bone tunnel after insertion but before deployment, easily actuated for permanent deployment, and deployable without requiring hammering of the anchor suture or threading of the bone tunnel.

In accordance with the present invention, it is believed that other modifications, variations and changes will be suggested to those skilled in the art in view of the teachings set forth herein. It is therefore understood that all such variations, modifications and changes are believed to fall within the scope of the present invention as defined by the appended claims.

What is claimed is:

1. A bone anchor for securing suture in a bone tunnel by engaging the bone tunnel wall, said anchor comprising:
    a body section;
    at least first and second bendably deformable wire legs having no significant resilience, each having a first end secured to said body section and an opposite pointed end suitable for penetrating bone tissue; and
    an engageable element projecting from said body section to permit the anchor to be grasped and positioned in the bone tunnel;
    wherein said anchor has a pre-deployment position in which said deformable wire legs are retracted in a dimension transversely of the bone tunnel axis to permit the anchor to be unimpededly inserted into and removed from the bone tunnel; and
    wherein said anchor, while in the bone tunnel, is capable of being deformably bent to a permanent deployment position in which said wire legs extend generally toward an opening of the bone tunnel at an acute angle to the bone tunnel wall to permit the pointed ends of the wire legs to penetrate the bone tunnel wall as the anchor is moved in a direction toward the tunnel opening.

2. The bone anchor of claim 1 further including:
    a deformably bendable wire having a twist section therein to define a loop at a location intermediate said first and second ends, said loop defining a proximal end of said anchor, said twist constituting at least part of said body section;
    said wire further comprising said first and second legs each having:
    an inner leg segment extending generally distally from said twist section;
    a knee segment in the form of a 180°-outward bend extending from the distal end of said inner leg segment; and
    an outer leg segment extending proximally from said knee segment and terminating in said pointed end;
    wherein, in said pre-deployment position, said knee segment is a bend through an angle of approximately 180°, and wherein for said deployment position said outer leg segments are deformably bendable outwardly about respective knee segments.

3. The bone anchor of claim 2 wherein said twist section is defined by bends at the proximal ends of said inner leg segments of approximately 90° each about one another.

4. The bone anchor of claim 2 wherein said loop has a generally elliptical configuration.

5. The bone anchor of claim 2 wherein said pointed ends of said legs are defined by bias cuts in said wire to provide points at the transversely outer side of each outer leg segment.

6. The bone anchor of claim 2 wherein said pointed ends of said legs are curved transversely outward.

7. The bone anchor of claim 2 further comprising:
    an anchor sleeve secured to said wire and constituting an additional part of said body section, said anchor sleeve having an open distal end, a hollow interior, and a proximal end wall with an aperture defined therethrough;
    wherein said wire is disposed with said twist section and said inner leg segments inside said sleeve, with said loop projecting proximally through said aperture, with said knees bent about the open distal end of said sleeve, and with said outer leg segments extending proximally along opposite sides of the outer surface of said sleeve.

8. The bone anchor of claim 7 further comprising wire leg relief means defined in said sleeve for receiving said outer leg segments at least partially recessed relative to the periphery of said sleeve in said pre-deployment position.

9. The bone anchor of claim 8 wherein said wire leg relief means comprises at least first and second channels defined longitudinally along the periphery of said sleeve for receiving said outer leg segments of said first and second wire legs, respectively.

10. The bone anchor of claim 9 further comprising suture relief means for permitting portions of a suture to pass transversely through said sleeve.

11. The bone anchor of claim 10 wherein said suture relief means comprises first and second spaced slots defined at different circumferential locations of said sleeve to permit a suture to pass through the hollow interior of said sleeve.

12. The bone anchor of claim 7 further comprising suture relief means for permitting portions of a suture to pass transversely through said sleeve.

13. The bone anchor of claim 12 wherein said suture relief means comprises first and second spaced slots defined at different circumferential locations of said sleeve to permit a suture to pass through the hollow interior of said sleeve.

14. A bone anchor for securing suture in a bone tunnel by engaging the bone tunnel wall, said anchor comprising:
   a body section;
   at least first and second bendable wire legs each having a first end secured to said body section and an opposite pointed end suitable for penetrating bone tissue;
   an engageable element projecting from said body section to permit the anchor to be grasped and positioned in the bone tunnel;
   wherein said anchor has a pre-deployment position in which said deformable wire legs are retracted in a dimension transversely of the bone tunnel axis to permit the anchor to be unimpededly inserted into and removed from the bone tunnel; and
   wherein said anchor, while in the bone tunnel, is capable of being bent to a deployment position in which said wire legs extend generally toward an opening of the bone tunnel at an acute angle to the bone tunnel wall to permit the pointed ends of the wire legs to penetrate the bone tunnel wall as the anchor is moved in a direction toward the tunnel opening;
   a bendable wire having a twist section therein to define a loop at a location intermediate said first and second ends, said loop defining a proximal end of said anchor, said twist constituting at least part of said body section;
   said wire further comprising said first and second legs each having:
   an inner leg segment extending generally distally from said twist section;
   a knee segment in the form of a 180°-outward bend extending from the distal end of said inner leg segment; and
   an outer leg segment extending proximally from said knee segment and terminating in said pointed end;
   wherein, in said pre-deployment position, said knee segment is a bend through an angle of approximately 180°, and wherein for said deployment position said outer leg segments are bendable outwardly about respective knee segments.

15. The bone anchor of claim 14 wherein said twist section is defined by bends at the proximal ends of said inner leg segments of approximately 90° each about one another.

16. The bone anchor of claim 14 wherein said loop has a generally elliptical configuration and constitutes said engageable element.

17. The bone anchor of claim 14 wherein said pointed ends of said legs are defined by bias cuts in said wire to provide points at the transversely outer side of each outer leg segment.

18. The bone anchor of claim 14 wherein said pointed ends of said legs are curved transversely outward.

19. The bone anchor of claim 14 further comprising:
   an anchor sleeve secured to said wire and constituting an additional part of said body section, said anchor sleeve having an open distal end, a hollow interior, and a proximal end wall with an aperture defined therethrough;
   wherein said wire is disposed with said twist section and said inner leg segments inside said sleeve, with said loop projecting proximally through said aperture, with said knees bent about the open distal end of said sleeve, and with said outer leg segments extending proximally along opposite sides of the outer surface of said sleeve.

20. The bone anchor of claim 19 further comprising wire leg relief means defined in said sleeve for receiving said outer leg segments at least partially recessed relative to the periphery of said sleeve in said pre-deployment position.

21. The bone anchor of claim 20 wherein said wire leg relief means comprises at least first and second channels defined longitudinally along the periphery of said sleeve for receiving said outer leg segments of said first and second wire legs, respectively.

22. The bone anchor of claim 21 further comprising suture relief means for permitting portions of a suture to pass transversely through said sleeve.

23. The bone anchor of claim 22 wherein said suture relief means comprises first and second spaced slots defined at different circumferential locations of said sleeve to permit a suture to pass through the hollow interior of said sleeve.

* * * * *